(12) United States Patent
Buscail et al.

(10) Patent No.: US 9,364,494 B2
(45) Date of Patent: Jun. 14, 2016

(54) SOMATOSTATIN 2 RECEPTOR (SST2), DEOXYCYTIDINE KINASE (DCK) AND URIDINE MONOPHOSPHATE KINASE (UMK) PANCREATIC GENE THERAPY

(75) Inventors: Louis Buscail, Toulouse (FR); Gérard Tiraby, Toulouse (FR); Fabienne Vernejoul, Toulouse (FR); Christiane Susini, Lanta (FR); Daniel Drocourt, St-Orens de Gameville (FR)

(73) Assignees: Institut National de la Sante et de la Recherche Medicale (INSERM), Paris (FR); Cayla, Toulouse (FR)

( * ) Notice: Subject to any disclaimer, the term of this patent is extended or adjusted under 35 U.S.C. 154(b) by 741 days.

(21) Appl. No.: 12/681,943

(22) PCT Filed: Oct. 10, 2008

(86) PCT No.: PCT/EP2008/063657
§ 371 (c)(1),
(2), (4) Date: Apr. 7, 2010

(87) PCT Pub. No.: WO2009/056434
PCT Pub. Date: May 7, 2009

(65) Prior Publication Data
US 2010/0222418 A1    Sep. 2, 2010

(30) Foreign Application Priority Data

Oct. 10, 2007    (EP) .................................... 07301447

(51) Int. Cl.
*A61K 48/00*    (2006.01)
*C07H 21/04*    (2006.01)
*A61K 38/45*    (2006.01)
*A61K 31/7068*  (2006.01)
*A61K 38/17*    (2006.01)
*A61K 47/48*    (2006.01)

(52) U.S. Cl.
CPC ......... *A61K 31/7068* (2013.01); *A61K 38/1796* (2013.01); *A61K 38/45* (2013.01); *A61K 47/48192* (2013.01); *C12Y 207/01074* (2013.01); *C12Y 207/04022* (2013.01)

(58) Field of Classification Search
CPC ........................... A61K 38/45; A61K 31/7968
USPC ............................................. 514/44; 536/23.1
See application file for complete search history.

(56) References Cited

U.S. PATENT DOCUMENTS

2007/0264241 A1 *  11/2007   Ekstrom et al. ............ 424/93.21

FOREIGN PATENT DOCUMENTS

| JP | 2007145761 | 6/2007 |
|---|---|---|
| WO | 2007011975 | 1/2007 |
| WO | 2007014162 | 2/2007 |
| WO | 2007102481 | 9/2007 |

OTHER PUBLICATIONS

Guida et al (Abstract, 1-2, 2009.*
Lamberts et al (Trends in Endocrinology & Metabolism, 13(10):451-457, 2002.*
Fillat et al (Cancers, 3, 368-395, 2011).*
Duran-Prado et al (Endocrinology 148: 411-421, 2007).*
Raiteri et al (Pharmacological Reviews, 58(2): 162-193, 2006).*
Coll et al (Human Gene Therapy, 10: 1659—1666, 1999).*
Tigerstedt et al (Thesis p. 1-93), 2009.*
Vernejoul, F., et al., Gene therapy based on gemcitabine chemosensitization suppresses pancreatic tumor growth, Mol Ther. Dec. 2006;14(6):758-67.
Gene therapy of pancreatic carcinoma based on gemcitabine chemosensitization using phosphorylating fusion gene transfer—10th Annual Meet Am Soc Gene Ther (ASGT) May 30-Jun. 3, Seattle 2007.
Vernejoul, F., et al., Antitumor effect of in vivo somatostatin receptor subtype 2 gene transfer in primary and metastatic pancreatic cancer models, Cancer Res. Nov 1, 2002;62(21):6124-31.
Carrere, N., et al., Characterization of the bystander effect of somatostatin receptor sst2 after in vivo gene transfer into human pancreatic cancer cells, Hum Gene Ther. Oct. 2005;16(10):1175-93.
Guillermet, J., et al., Somatostatin receptor subtype 2 sensitizes human pancreatic cancer cells to death ligand-induced apoptosis, Proc Natl Acad Sci U S A. Jan. 7, 2003;100(1):155-60.
Benali, N., et al., Inhibition of growth and metastatic progression of pancreatic carcinoma in hamster after somatostatin receptor subtype 2 (sst2) gene expression and administration of cytotoxic somatostatin analog AN-238, Proc Natl Acad Sci U S A. Aug. 1, 2000;97(16):9180-5.

(Continued)

*Primary Examiner* — Deborah Crouch
*Assistant Examiner* — Magdalene Sgagias
(74) *Attorney, Agent, or Firm* — Whitham, Curtis & Cook, P.C.

(57) ABSTRACT

The present invention concerns products containing (i) at least one nucleic acid sequence coding for the human somatostatin 2 receptor protein (sst2) having the sequence SEQ ID NO: 1, ortholog or derivative thereof, (ii) at least one nucleic acid sequence coding for the human deoxycytidine kinase protein (dck) having the sequence SEQ ID NO:2, ortholog or derivative thereof, (iii) at least one nucleic acid sequence coding for the human uridine monophosphate kinase protein (umk) having the sequence SEQ ID NO: 3 ortholog or derivative thereof, and (iv) gemcitabine, as a combined preparation for simultaneous, separate, or sequential use for treating cancer in a subject.

13 Claims, 2 Drawing Sheets

(56) References Cited

OTHER PUBLICATIONS

Delesque, N., et al., sst2 somatostatin receptor expression reverses tumorigenicity of human pancreatic cancer cells, Cancer Res. Mar. 1, 1997;57(5):956-62.

Edgar, Robert C., Muscle: multiple sequence alignment with high accuracy and high throughput, Nucleic Acids Res. Mar. 19, 2004;32(5):1792-7.

Hecht, J. R., et al., A phase I/II trial of intratumoral endoscopic ultrasound injection of ONYX-015 with intravenous gemcitabine in unresectable pancreatic carcinoma, Clin Cancer Res. Feb. 2003;9(2):555-61.

Pearson, W. R., et al., Improved tools for biological sequence comparison, Proc Natl Acad Sci U S A. Apr. 1988;85(8):2444-8.

Wu, G. Y., et al., Receptor-mediated gene delivery and expression in vivo, J Biol Chem. Oct. 15, 1988;263 (29):14621-4.

Rosenberg "Treatment of pancreatic cancer. Promises and problems of tamoxifen, somatostatin analogs, and gemcitabine.," International Journal of Pancreatology (1997) 22(2):81-93.

Onkologie (2000) 23(7):67, 0247.

* cited by examiner

US 9,364,494 B2

SOMATOSTATIN 2 RECEPTOR (SST2), DEOXYCYTIDINE KINASE (DCK) AND URIDINE MONOPHOSPHATE KINASE (UMK) PANCREATIC GENE THERAPY

Cross-Reference To Related Applications

This application is the U.S. National Stage filing of International Application Serial No. PCT/EP2008/063657 filed Oct. 10, 2008, which claims priority to European Application No. 07301447.4 filed Oct. 10, 2007, each of which is incorporated herein by reference in its entirety.

FIELD OF THE INVENTION

The invention relates to the field of cancer, and in particular to a new products, compositions, plasmid vector and methods for cancer therapy.

BACKGROUND OF THE INVENTION

Among cancer, pancreatic cancer is one of the most aggressive and devastating human malignancies. Its aggressiveness is illustrated by the fact that the number of estimated pancreatic cancer cases and number of pancreatic cancer-related deaths are almost identical with a minimal 5-year survival rate of 2%. Pancreatic cancer ranks at the fifth leading cause of cancer-related deaths in Western countries. So far, neither early detection nor treatment of advanced disease is possible: 85% of lesions are unresectable at the time of diagnosis, resulting in a median survival time of 4-5 months.

These dismal statistics are mainly consistent with the propensity of these tumors to metastasize when small and undetectable, and the intrinsic resistance of pancreatic cancer cells to cytotoxic agents and radiotherapy.

As another aggressive cancer, hepatocellular carcinoma (hepatocarcinoma, HCC) is the most common primary malignancy of the liver and the fourth most common cancer worldwide with an incidence of 1,000,000 new cases per year. It represents the $3^{rd}$ cause of death by cancer in the world. In France, as in other industrialized countries, its incidence is rising steadily due to the hepatitis C virus pandemic. HCC develops from cirrhosis: the 5-year probability for cirrhotic patients to develop HCC is almost 20%. The three main curative therapeutic modalities currently used for HCC are hepatic resection, percutaneous destruction of the tumor (radiofrequency) and orthotopic liver transplantation. These options may be used in patients with so called <<small>> HCC (<5 cm) with good results (70% 5 year survival and <25% recurrence rate for transplantation). Unfortunately, such therapeutic options are only accessible to less than 50% of the patients diagnosed with HCC. Therefore, the bulk of patients cannot benefit from curative therapeutic options because of large tumor size or underlying liver disease. For these reasons, new diagnosis modalities and therapies are needed. Up to now, no chemotherapy is efficient and thus indicated in HCC.

Consequently, there is an urgent need for therapies to treat cancer, like pancreatic cancer or hepatocellular cancer, and metastatic cancer specifically, that are more effective than current regimens.

SUMMARY OF THE INVENTION

In a first aspect, the present invention relates to products containing:
 (i) at least one nucleic acid sequence coding for the human somatostatin 2 receptor protein (SST2) having the sequence SEQ ID NO:1, ortholog or derivative thereof,
 (ii) at least one nucleic acid sequence coding for the human deoxycytidine kinase protein (DCK) having the sequence SEQ ID NO:2, ortholog or derivative thereof,
 (iii) at least one nucleic acid sequence coding for the human uridine monophosphate kinase protein (UMK) having the sequence SEQ ID NO:3, ortholog or derivative thereof, and
 (iv) gemcitabine,
 as a combined preparation for simultaneous, separate, or sequential use for treating cancer in a subject.

In a second aspect, the present invention relates to a method for treating cancer comprising the step of simultaneously, separately, or sequentially administrating to a subject in need thereof a therapeutically effective amount of:
 (i) at least one nucleic acid sequence coding for the human somatostatin 2 receptor protein (SST2) having the sequence SEQ ID NO: 1, ortholog or derivative thereof,
 (ii) at least one nucleic acid sequence coding for the human deoxycytidine kinase protein (DCK) having the sequence SEQ ID NO: 2, ortholog or derivative thereof,
 (iii) at least one nucleic acid sequence coding for the human uridine monophosphate kinase protein (UMK) having the sequence SEQ ID NO: 3, ortholog or derivative thereof, and
 (iv) gemcitabine.

In a third aspect, the present invention relates to a pharmaceutical composition comprising:
 (i) at least one nucleic acid sequence coding for the human somatostatin 2 receptor protein (SST2) having the sequence SEQ ID NO: 1, ortholog or derivative thereof,
 (ii) at least one nucleic acid sequence coding for the human deoxycytidine kinase protein (DCK) having the sequence SEQ ID NO: 2, ortholog or derivative thereof,
 (iii) at least one nucleic acid sequence coding for the human uridine monophosphate kinase protein (UMK) having the sequence SEQ ID NO: 3, ortholog or derivative thereof, and
 (iv) optionally a pharmaceutically acceptable carrier.

In a forth aspect, the present invention finally relates to a plasmid vector having the sequence SEQ ID NO:11, and comprising nucleic acid sequences coding for the *Homo sapiens* somatostatin 2 receptor protein and for a polypeptide comprising the two proteins *Homo sapiens* deoxycytidine kinase protein (dck) and *Homo sapiens* uridine monophosphate kinase protein (umk) linked by the cleavable FMDV (Foot-and-Mouth-Disease virus) 2A peptide.

BRIEF DESCRIPTION OF THE DRAWINGS

The FIG. 1 shows the schematic map of pHNeo Sst2 DCK::UMK (7548 pb) plasmid (SEQ ID NO: 11).

The FIG. 2 shows the schematic map of pHDuo14 LGFP-dckumk2A (7368 pb) plasmid vector.

DESCRIPTION OF THE PREFERRED EMBODIMENTS

Figure 1:
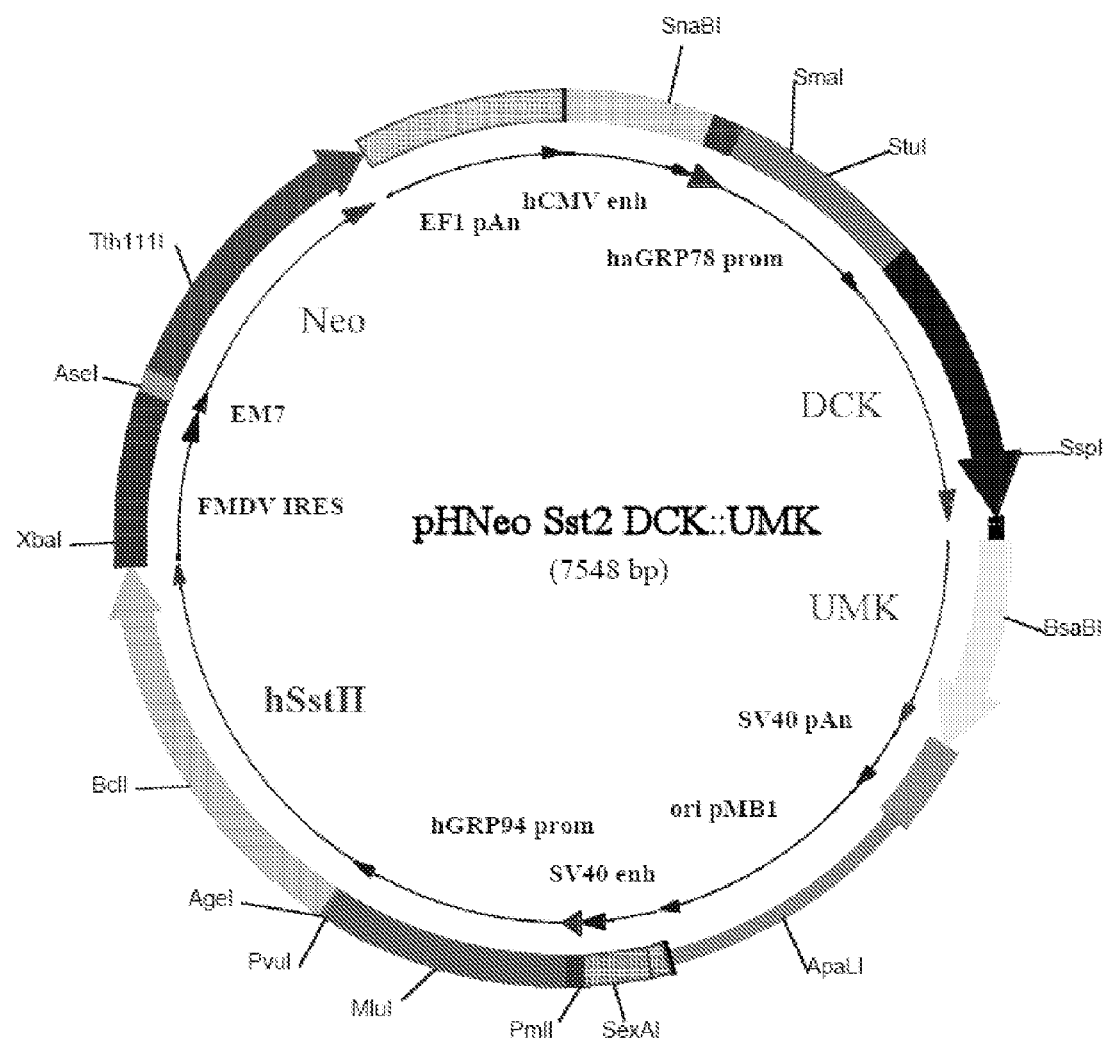

In the sense of the present application, the cancer is preferably a metastatic cancer, like the pancreatic cancer and hepatocellular carcinoma, and most preferably an exocrine pancreatic cancer.

Metastase corresponds to the process by which a cancer spreads from the place at which it first arose as a primary tumor to distant locations in the body. Since this process is very particular in cancer progression, it is generally necessary to use specific regimen in order to inhibit metastazing.

The inventors have established that the combined intra-tumoral injection of an expression vector coding for SST2, DCK and UMK associated with a gemcitabine administration results in an extensive and surprising decrease of metastasis sites.

Accordingly, and in a preferred embodiment, the present invention is directed to the inhibition of tumor spread out—i.e., the inhibition of tumor metastazing—.

The term subject refers to a mammal and preferably to a human.

As used herein, Gemcitabine refers to Gemcitabine HCl/Chlorhydrate, marketed by ELI LILLY under the trademark GEMZAR®, which is a nucleoside analogue that exhibits antitumor activity and belongs to a general group of chemotherapy drugs known as antimetabolites. Gemcitabine prevents cells from producing DNA and RNA by interfering with the synthesis of nucleic acids, thus stopping the growth of cancer cells and causing them to die.

Gemcitabine which is disclosed in International PCT application WO 97/21719 is a synthetic glucoside analog of cytosine, which is chemically described as 1-(2'-Deoxy-2',2'-difluoro-[beta]-D-ribofuranosyl)-4-aminopyrimidin-2-one hydrochloride or 2'-deoxy-2',2'-difluorocytidine monohydrochloride [beta] isomer).

As used herein, the term "orthologs" refers to proteins in different mammal species than the proteins SEQ ID NO: 1, SEQ ID NO: 2 or SEQ ID NO: 3 in *Homo sapiens* that evolved from a common ancestral gene by speciation. One of skill in the art in view of the specification and of its general knowledge can simply identify such orthologs.

As an example of such orthologs, one can cite the somatostatin 2 receptor proteins in *Mus musculus* (SEQ ID NO: 4) and in *Rattus norvegicus* (SEQ ID NO: 5), the deoxycytidine kinase protein in *Mus musculus* (SEQ ID NO: 6), in *Rattus norvegicus* (SEQ ID NO: 7) and in *Bos Taurus* (SEQ ID NO: 8), or the uridine monophosphate kinase protein in *Rattus norvegicus* (SEQ ID NO: 9).

As used herein, the term "derivatives'" refer to a polypeptide having a percentage of identity of at least 80% with complete SEQ ID NO: 1, SEQ ID NO: 2 or SEQ ID NO: 3, or orthologs thereof, preferably of at least 90%, as an example of at least 95%, and more preferably of at least 99%.

As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids sequences are usually realized by comparing these sequences that have been previously align according to the best alignment; this comparison is realized on segments of comparison in order to identify and compared the local regions of similarity. The best sequences alignment to perform comparison can be realized, beside by a manual way, by using the global homology algorithm developed by SMITH and WATERMAN (*Ad. App. Math.*, vol. 2, p:482, 1981), by using the local homology algorithm developed by NEDDLEMAN and WUNSCH (*J. Mol. Biol.*, vol. 48, p:443, 1970), by using the method of similarities developed by PEARSON and LIPMAN (*Proc. Natl. Acd. Sci. USA*, vol. 85, p:2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., *Nucleic Acids Research*, vol. 32, p:1792, 2004). To get the best local alignment, one can preferably used BLAST software, with the BLOSUM 62 matrix, or the PAM 30 matrix. The identity percentage between two sequences of amino acids is determined by comparing these two sequences optimally aligned, the amino acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

According to another preferred embodiment, the *Homo sapiens* deoxycytidine kinase protein (dck) having the sequence SEQ ID NO: 2, ortholog or derivative thereof, and the *Homo sapiens* uridine monophosphate kinase protein (umk) having the sequence SEQ ID NO: 3, ortholog or derivative thereof, are encoded by a single nucleic acid sequence.

Preferably, said at least one nucleic acid sequence encodes for a polypeptide comprising the two proteins *Homo sapiens* deoxycytidine kinase protein (dck) and *Homo sapiens* uridine monophosphate kinase protein (umk) linked by the cleavable FMDV (Foot-and-Mouth-Disease virus) 2A peptide, which polypeptide has the sequence SEQ ID NO: 10.

According to still another preferred embodiment, the nucleic acids encoding somatostatin 2 receptor protein (sst2), deoxycytidine kinase protein (dck), and/or uridine monophosphate kinase protein (umk) are operatively linked to a gene expression sequence, which directs the expression of nucleic acids within an eukaryotic cell. The "gene expression sequence" is any regulatory nucleotide sequence, such as a promoter sequence or promoter-enhancer combination, which facilitates the efficient transcription and translation of the nucleic acid to which it is operatively linked. The gene expression sequence may, for example, be a mammalian or viral promoter, such as a constitutive or inducible promoter. In the plasmid designed for the present concept, the two genes (sst2 and dck::umk fusion) are under the control of two different promoters sensitive to hypoxia (basal activity of each promoter is dramatically increased within the tumor due to the hypoxic area present in pancreatic carcinoma tissues): promoter region from GRP78 gene (Glucose-regulated protein 78) and promoter region from GRP94 gene (Glucose-regulated protein 94) for dck::umk fusion and sst2 respectively. Constitutive mammalian promoters include, but are not limited to, the promoters for the following genes: hypoxanthine phosphoribosyl transferase (HPTR), adenosine deaminase, pyruvate kinase, beta.-actin promoter, muscle creatine kinase promoter, human elongation factor promoter and other constitutive promoters. Exemplary viral promoters which function constitutively in eukaryotic cells include, for example, promoters from the simian virus (e.g., SV40), papilloma virus, adenovirus, human immunodeficiency virus (HIV), cytomegalovirus (CMV), Rous sarcoma virus (RSV), hepatitis B virus (HBV), the long terminal repeats (LTR) of Moloney leukemia virus and other retroviruses, and the thymidine kinase promoter of herpes simplex virus. Others constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Others inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined antigen nucleic acid. The gene expression sequences optionally include enhancer sequences or upstream activator sequences as desired.

As used herein, nucleic acid sequences encoding the proteins sst2, dck and umk, and the gene expression sequence are said to be "operably linked" when they are covalently linked in such a way as to place the expression or transcription and/or translation of the protein coding sequences under the influence or control of the gene expression sequence. Two DNA sequences are said to be operably linked if induction of a promoter in the 5' gene expression sequence results in the transcription of the proteins and if the nature of the linkage between the two DNA sequences does not (1) result in the introduction of a frame-shift mutation, (2) interfere with the ability of the promoter region to direct the transcription of the polypeptide of the invention, or (3) interfere with the ability of the corresponding RNA transcript to be translated into a protein.

The nucleic acid coding for the proteins sst2, dck and umk may be delivered in vivo alone or in association with a vector. In its broadest sense, a "vector" is any vehicle capable of facilitating the transfer of the nucleic acid coding for the proteins sst2, dck and umk to the cells. Preferably, the vector transports the nucleic acid to cells with reduced degradation relative to the extent of degradation that would result in the absence of the vector. In general, the vectors useful in the invention include, but are not limited to, plasmids, phagmids, viruses, other vehicles derived from viral or bacterial sources that have been manipulated by the insertion or incorporation of the peptidic antagonist nucleic acid sequences.

Preferred viral vectors for certain applications are the adeno-viruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

The nucleic acid vector can include selectable markers that are active both in bacteria and in mammalian cells.

According to still another embodiment, the previously described nucleic acid sequences correspond to "naked DNA" like plasmids, cosmids or phagemids, preferably to at least one plasmid vector, and most preferably to one plasmid vector.

Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In another preferred embodiment, the nucleic acid encoding for the proteins sst2, dck and umk are comprised in a plasmid vector.

Advantageously, said plasmid vector has the sequence SEQ ID NO:11 and comprises nucleic acid sequences coding for the *Homo sapiens* somatostatin 2 receptor protein and for a polypeptide comprising the two proteins *Homo sapiens* deoxycytidine kinase protein (dck) and *Homo sapiens* uridine monophosphate kinase protein (umk) linked by the cleavable FMDV (Foot-and-Mouth-Disease virus) 2A peptide.

Such "naked DNA" or plasmid(s) vector(s) is preferably associated with non-lipid cationic polymers (WU and WU, *J. Biol. Chem.*, vol. 263, p: 14621-4, 1988), such as polyethylenimine (PEI) as disclosed in EP 0770140 or liposomes (BRIGHMAN et al., *Am. J. Med. Sci.*, vol. 298, p: 278-81, 1989) to form complexes enhancing cellular uptake.

Advantageously, such naked DNA or plasmid(s) vector(s) is associated with non-lipid cationic polymers, preferably with polyethylenimine (PEI) as disclosed in EP 0770140.

In a specific embodiment, the products of the invention further comprise at least one pharmaceutically acceptable carrier.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E.W. Martin.

The nucleic acid sequences or the nucleic acid vectors or Gemcitabine may be solubilized in a buffer or water or incorporated in emulsions and microemulsions. Suitable buffers include, but are not limited to, phosphate buffered saline $Ca^{++}/Mg^{++}$ free (PBS), phosphate buffered saline (PBS), normal saline (150 mM NaCl in water), Tris buffer and surfactants.

According to still another specific embodiment, the nucleic acid sequences described previously are administrated by intra-tumoral injection, preferably by intra-tumoral endoscopic ultrasound injection (i.e., echoendoscopy) as disclosed in HECHT et al. (*Clin. Cancer Res.*, vol. 9, p:555-61, 2003) as an example.

According to another specific embodiment, gemcitabine is administrated by intravenous route.

According to the present invention, an "effective amount" of a composition is one which is sufficient to achieve a desired biological effect, in this case inducing apoptosis in tumor cells and inhibiting metastazing. It is understood that the effective dosage will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges. However, the preferred dosage can be tailored to the individual subject, as is understood and determinable by one of skill in the art, without undue experimentation.

As an example, an effective amount of a plasmid vector having the sequence SEQ ID NO:11 for an intra-tumoral injection depends on the tumor volume and is comprised between 1 and 1,000 µg of DNA per $cm^3$ of tumor, preferably between 5 and 500 µg/$cm^3$, more preferably between 8 and 500 µg/$cm^3$.

As an example, an effective amount of gemcitabine corresponds to an administration of gemcitabine at 1000 mg/$m^2$ (of patient surface) per day. Such an administration is realized once a week during four consecutive weeks.

Surprisingly, the inventors have established that the intra-tumoral injection of the plasmid having the sequence SEQ ID NO:11 enables to obtain a tumor regression in combination with a dose of gemcitabine lower than the dose used for conventional pancreatic cancer treatment (⅔ of the normal gemcitabine dose).

Thus, in a preferred embodiment, an effective amount of gemcitabine corresponds to a dose of equal or less than 750 mg/$m^2$ per day. Such an administration is realized once a week during four consecutive weeks as previously.

Preferably, an effective amount of gemcitabine corresponds to a dose of 500 mg/$m^2$ per day, and once a week during four consecutive weeks as previously.

In the following, the invention is described in more detail with reference to nucleic acid sequences and the examples. Yet, no limitation of the invention is intended by the details of the examples. Rather, the invention pertains to any embodiment, which comprises details which are not explicitly mentioned in the examples herein, but which the skilled person finds without undue effort.

EXAMPLES

I Treatment of Pancreas Cancer 1) sst2 and DCK:UMK/Gemcitabine Combination Sensitizes Pancreatic Cancer Cells to Death In Vitro:

BxPC-3 and MiaPaca-2 cells, derived from human pancreatic ductal carcinoma (DELESQUE et al., *Cancer Research*, vol. 57, p:956-962, 1997) were maintained in RPMI 1640 medium (INVITROGEN) supplemented with 5% foetal calf serum (FCS; INVITROGEN), fungizone (INVITROGEN), antibiotics (streptomycin, penicillin, SIGMA), L-glutamine (INVITROGEN), and an anti-mycoplasma reagent (PLASMOCIN™, CAYLA).

Figure 2:
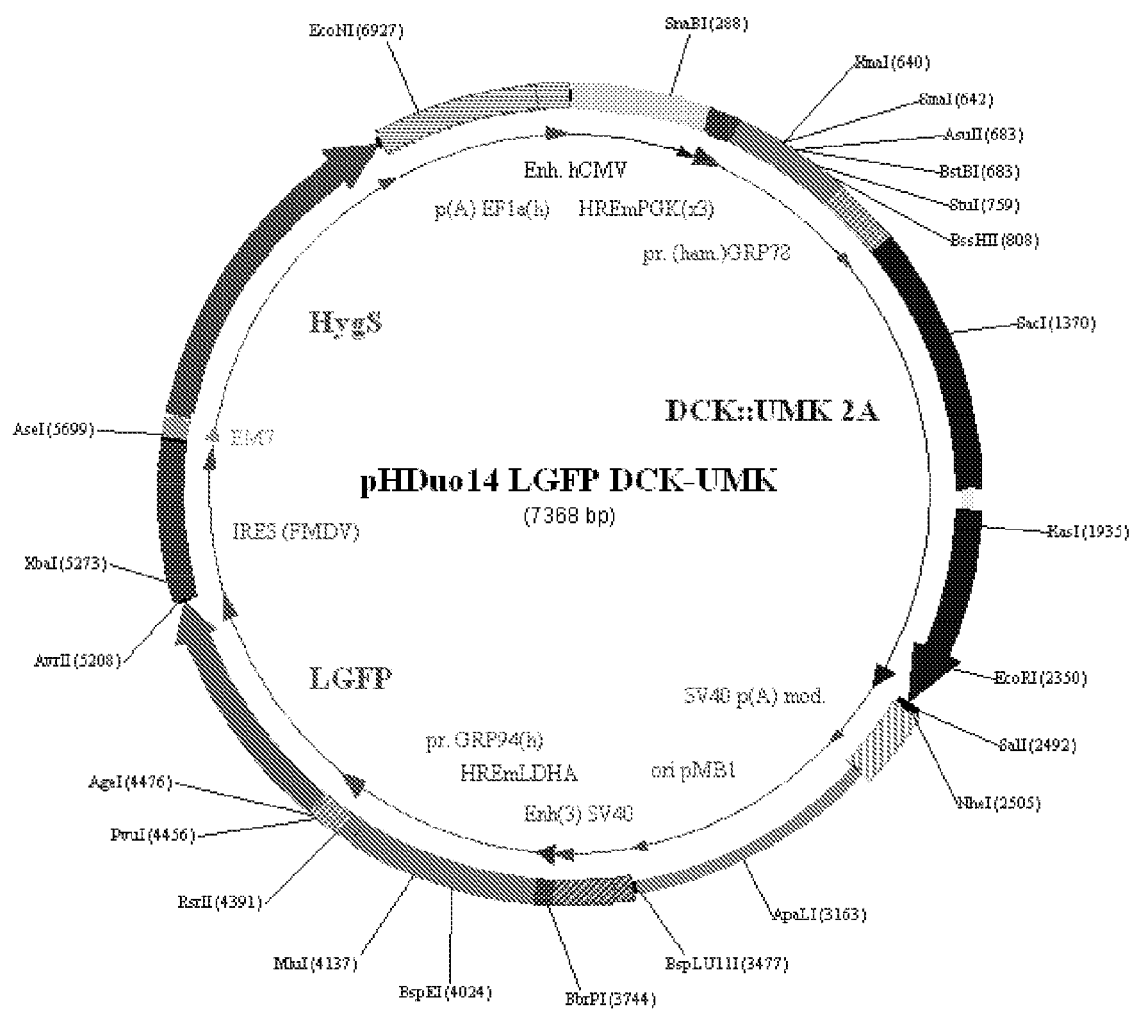

Human pancreatic cancer cells were plated in 35-mm-diameter dishes at $50 \times 10^3$ cells/ml (2 ml per dish) in RPMI 1640 containing 5% FCS. After a 12 h attachment phase, cells were transfected with 5 µg of a mock vector or with 5 µg of plasmid comprising a fusion cDNA DCK:UMK comprising the self cleaving FMDV 2A peptide inserted between DCK and UMK cDNAs with (pHNeo Sst2 DCK::UMK; FIG. 1) or without (pHDuo14 LGFP DCK-UMK; FIG. 2) the human sst2 cDNA (CAYLA) using linear polymers of ethyleneimine (PEI or L-PEI) with a mean molecular mass of 22 kDa (POLYPLUS-Transfection) (ratio PEI nitrogen to DNA phosphate N/P=8 to 10). PEI-DNA complexes were prepared in 5% (w/v) glucose. After 24 h of cell culture in RPMI 1640 containing 5% FCS, medium were replaced by fresh medium supplemented or not with increasing concentrations of gemcitabine (0.05 to 5 µg/ml) and cell counting was performed after 48 h of culture.

The results show that the combined expression of UMK, DCK and of SST2 sensitizes tumor cells to gemcitabine.

2) The Combination of sst2 and DCK:UMK/Gemcitabine Inhibits Growth of Pancreatic Tumors In Vivo:

PC1.0 cells, derived from a pancreatic ductal carcinoma induced by N-nitrosobis(2-oxopropyl)amine in Syrian golden hamsters (BENALI et al., *Proc. Natl. Acad. Sci. USA*, vol. 97, p:9180-9185, 2000) were maintained in RPMI 1640 medium (INVITROGEN) supplemented with 5% foetal calf serum (FCS; INVITROGEN), fungizone (INVITROGEN), antibiotics (streptomycin, penicillin, SIGMA), L-glutamine (INVITROGEN), and an anti-mycoplasma reagent (PLASMOCIN™, CAYLA).

For stable transfection, PC1.0 cells were plated in 60-mm diameter dishes ($2 \times 10^5$ cells per dish) in 4 ml of RPMI 1640 containing 5% FCS. After a 12 h attachment phase, cells were transfected with 5 µg of the mock vector (VERNEJOUL et al., Cancer Research, vol. 62, p:6124-31, 2002), of plasmid comprising a fusion cDNA DCK:UMK comprising the self cleaving FMDV 2A peptide inserted between DCK and UMK cDNAs (pHNeo Sst2 DCK::UMK; FIG. 1) or without (pHDuo14 LGFP DCK-UMK; FIG. 2) the human sst2 cDNA (CAYLA) using lipid cationic molecule (LyoVec™, CAYLA) (ratio lipid to DNA w/w=1:6). Stable clonal populations were selected in the presence of 0.4 to 0.6 mg/ml zeocin. Stable transfectants were then cultured in RPMI 1640 medium containing 5% SVF and 0.3 mg/ml zeocin.

Five-week-old male Syrian golden hamsters (GANNAT) were acclimatized in a temperature-controlled room under a 12-h light/12-h dark schedule and receive pelleted diet and water.

PC1.0 cells or mixed populations of PC1.0.DCK:UMK.SST2 and PC1.0 wildtype cells were orthotopically implanted into hamsters. Briefly, under pentobarbital anaesthesia and after a small laparotomy, $5 \times 10^5$ PC1.0 cells resuspended in 0.1 ml of FCS-free RPMI medium 1640 were injected into the tail of the pancreas under microscope by means of a sterile 29G lymphography catheter set.

On day 7, during the exponential phase of primary pancreatic tumors, the animals were treated with gemcitabine or vehicle, NaCl 0.9%. Gemcitabine was administrated intraperitoneally three times at a dose of 120 mg/kg/day at days 9, 11 and 13 post-implantation.

On day 15, the results have shown a complete recession of the tumor for the animals expressing DCK, UMK and SST2, whereas the gemcitabine only slow down the tumor progression in the animals which do not express these proteins.

3) In Vivo Transfer of the Combination of sst2 and DCK:UMK/Gemcitabine

PC1.0 cells were orthotopically implanted into hamsters as described previously. Eight days later, after median laparatomy under anaesthesia, tumor volume was measured and an intra-tumoral gene transfer was performed using in vivo PEI 22-kDa (ratio PEI nitrogen to DNA phosphate N/P=10) in 5% glucose. PEI/DNA complexes were then injected into exponentially growing tumors using a sterile 29-Gauge lymphography catheter set with a flow rate of 25 µl/min. A total of 25 to 50 µg of DCK:UMK or DCK:UMK:SST2 expression vectors were injected. Animals were then i.p injected with NaCl 0.9% or gemcitabine (80 to 120 mg/kg/day every three days). Tumor volumes and progression were evaluated after sacrifice at day 15 post-cell implantation.

The tumor progression after ex vivo and in vivo gene expression and metastasis evolution results are listed in the following tables I and II.

TABLE I

Tumor progression

|  | Tumor progression (percentage) |
|---|---|
| No DNA, No Gemcitabine | +800 to 1060 |
| Gemcitabine, No DNA | +150 to 378 |
| DCK:UMK:SST2 | +200 |
| DCK:UMK, Gemcitabine | −60 |
| DCK:UMK:SST2, Gemcitabine | −15 to −30 |

TABLE II

Number of metastatic sites

|  | Number of metastatic sites (percentage) |
|---|---|
| No DNA, No Gemcitabine (control) | 100 |
| DCK:UMK | 82 |
| DCK:UMK:SST2 | 100 |
| DCK:UMK, Gemcitabine | 47.6 |
| DCK:UMK:SST2, Gemcitabine | 12.2 |

The results established that the expression of the fusion DCK:UMK in some tumor cells in combination with an administration of gemcitabine results in tumor regression (table I).

The results established also that the intra-tumor injection of fusion DCK::UMK and SST2 in combination to gemcitabine results in tumor regression even at a lower dose than normally applied: 120 mg/kg applied in hamster corresponds to a dose of 1000 mg/m² in human. Thus 80 mg/kg of gemcitabine in hamster (that also induced a tumor regression when co-administered with DCK::UMK and SST2) correspond to 2/3 of regular dose applied in human. The intra-tumor injection of DCK::UMK and SST2 allows reducing the dose of gemcitabine without alteration of the antitumor effect.

The results also established that the expression of SST2 (DCK:UMK:SST2 without gemcitabine; table II) does not inhibit tumor metastazing, whereas the combined expression of DCK:UMK with gemcitabine treatment inhibit tumor metastazing by two fold. Unexpectedly, the coexpression of SST2 with DCK:UMK associated with gemcitabine treatment results in a strong inhibition of tumor metastazing—i.e. nearly ten fold reduction—.

Finally, the results have established that the injection of plasmids has never resulted in an immediate or delayed allergic reaction in any of the treated animals. Moreover, the intra-tumoral administration of the therapeutic vector coexpressing SST2 and DCK:UMK do not result in any animal in a general toxicity—i.e., survival—, a regional toxicity—i.e., stomach, liver, spleen or peritoneum—or in a local toxicity—i.e., normal adjacent pancreas—.

4) Human Gene Therapy Using the Combination of sst2 and DCK:UMK/Gemcitabine 24 patients suffering from non resecable adenocarcinoma pancreatic cancer are selected.

125 µg, 250 µg, 500 µg, and 1 mg of pHNeo Sst2 DCK::UMK plasmid (CAYLA, SEQ ID NO: 11) are complexed in 5% glucose with linear polyethyleneimine derivative (jet-PEI™, POLYPLUS, ratio PEI nitrogen to DNA phosphate N/P=10) according to the manufacturer instruction. The resulting complexes are lyophilised in 5 ml vial. Preliminary to the patient injection, the complexes are reconstituted in 2.5 ml of sterile water for injection and maintained at room temperature during 10 minutes before use.

Four groups of 6 patients are subjected to an intra-tumoral administration of the complexes comprising 125 µg, 250 µg, 500 µg, and 1 mg of DNA respectively (escalating dose starting by the lower dose i.e. the first 6 patients receive 125 µg, the new 6 patients 250 µg and following). Said administration step is realized by endoscopic ultrasound injection that is performed at day one.

On day 3, the treated patients are perfused for an intravenous administration of 1000 mg/m² of gemcitabine (GEMZAR®) during 30 minutes. Similar perfusions are realized on days 10, 17, and 24 following the plasmid intra-tumoral administration.

The daily evolution of the tumor progression is established for all the patients and, on day 29, a second intra-tumoral plasmid administration is realized on the four groups of 6 patients as described previously.

On days 31, 38, and 45 the treated patients are perfused for an intravenous gemcitabine administration as described previously.

The daily evolution of the tumor progression is established for all the patients until day 60.

The average of human pancreas tumor volume is 32 cm³±8. Considering the experiences realized in animals and on a tumor of 30 cm³, the dose of 125 µg of DNA (4.17 µg/cm³) should be inefficient for inhibiting tumor progression, whereas the dose of 250 µg of DNA (8.35 µg/cm³) and greater should be efficient for treating pancreas cancer and for inhibiting the metastazing of pancreas cancer.

II Treatment of Other Cancers 1) sst2 and DCK:UMK/Gemcitabine Combination Sensitizes Hepatocellular Carcinoma and Hepatoma Cells to Death In Vitro:

HuH7 cells, derived from human hepatocellular carcinoma, and HepG2 cells derived from hepatoma were plated in 35-mm-diameter dishes at 50×10³ cells/ml (2 ml per dish) in DMEM culture medium. After a 12 h attachment phase, cells were transfected with 5 µg of a mock vector or with 5 µg of plasmid comprising a fusion cDNA DCK:UMK comprising the self cleaving FMDV 2A peptide inserted between DCK and UMK cDNAs with (pHNeo Sst2 DCK::UMK; FIG. 1) the human sst2 cDNA (CAYLA) using linear polymers of ethyleneimine (PEI or L-PEI) with a mean molecular mass of 22 kDa (POLYPLUS-Transfection) (ratio PEI nitrogen to DNA phosphate N/P=8 to 10). PEI-DNA complexes were prepared in 5% (w/v) glucose. After 24 h of cell culture in DMEM containing 10% FCS, medium were replaced by fresh medium supplemented or not with increasing concentrations of gemcitabine (0.05 to 5 µg/ml) and cell counting was performed after 48 h of culture.

The results show that the combined expression of UMK, DCK and of SST2 drastically sensitizes tumor cells derived from HCC and hepatoma to gemcitabine.

The invention claimed is:

1. A method for treating pancreatic cancer comprising administering intratumorally or orthotopically to a pancreatic tumor in a patient:
   (i) at least one nucleic acid sequence encoding for a somatostatin 2 receptor protein (sst2) comprising the amino acid sequence SEQ ID NO: 1, SEQ ID NO: 4, or SEQ ID NO: 5;
   (ii) at least one nucleic acid sequence encoding for a deoxycytidine kinase protein (dck) comprising the amino acid sequence SEQ ID NO: 2, SEQ ID NO: 6, SEQ ID NO: 7, or SEQ ID NO: 8;
   (iii) at least one nucleic acid sequence encoding for a uridine monophosphate kinase protein (umk) comprising the amino acid sequence SEQ ID NO: 3 or SEQ ID NO: 9, and
   (iv) gemcitabine, wherein said nucleic acids are expressed, and wherein expression of said nucleic acids and administration of gemcitabine results in recession of said pancreatic tumor in the patient.

2. The method of claim 1, wherein said administering inhibits metastasis of said pancreatic tumor in the patient.

3. The method of claim 1, wherein said patient is a human.

4. The method of claim 1, wherein the at least one nucleic acid sequence encoding dck in (ii) is the amino acid sequence set for in SEQ ID NO: 2 and the at least one nucleic acid sequence encoding umk in (iii) is the amino acid sequence SEQ ID NO: 3, and wherein the nucleic acids of (ii) and (iii) are administered simultaneously.

5. The method of claim 4, wherein the at least one nucleic acid of (ii) and (iii) are linked by a nucleic acid encoding a cleavable Foot-and-Mouth-Disease virus (FMDV) 2 A peptide, thereby encoding the amino acid sequence set forth in SEQ ID NO: 10.

6. The method of claim 1, wherein the at least one nucleic acids of (i)-(iii) are present within one expression vector.

7. The method of claim 6, wherein the one expression vector comprise a nucleic acid having the sequence set forth in SEQ ID NO: 11.

8. The method of claim 6, wherein said expression vector is complexed with a non-lipid cationic polyethylenimine (PEI) polymers.

9. A pharmaceutical composition comprising an expression vector comprising:
   (i) at least one nucleic acid sequence encoding for a somatostatin 2 receptor protein (sst2) comprising the amino acid sequence SEQ ID NO: 1, SEQ ID NO: 4, or SEQ ID NO: 5;
   (ii) at least one nucleic acid sequence encoding for a deoxycytidine kinase protein (dck) comprising the amino acid sequence SEQ ID NO: 2, SEQ ID NO: 6, SEQ ID NO: 7, or SEQ ID NO: 8;
   (iii) at least one nucleic acid sequence encoding for a uridine monophosphate kinase protein (umk) comprising the amino acid sequence SEQ ID NO: 3 or SEQ ID NO: 9.

10. The pharmaceutical composition according to claim 9, wherein the one expression vector comprise a nucleic acid having the sequence set forth in SEQ ID NO:11, wherein the at least one nucleic acid of (ii)-(iii) are linked by a nucleic acid encoding a cleavable Foot-and-Mouth-Disease virus (FMDV) 2 A peptide, thereby encoding the amino acid sequence set forth in SEQ ID NO: 10.

11. The pharmaceutical composition according to claim 10, wherein said expression vector is complexed with a non-lipid cationic polyethylenimine (PEI) polymers.

12. A plasmid vector comprising one expression vector comprising a nucleic acid having the sequence set forth in SEQ ID NO:11, which comprises:
   (i) at least one nucleic acid sequence encoding for a somatostatin 2 receptor protein (sst2) comprising the amino acid sequence SEQ ID NO: 1, SEQ ID NO: 4, or SEQ ID NO: 5;
   (ii) at least one nucleic acid sequence encoding for a deoxycytidine kinase protein (dck) comprising the amino acid sequence SEQ ID NO: 2, SEQ ID NO: 6, SEQ ID NO: 7, or SEQ ID NO: 8;
   (iii) at least one nucleic acid sequence encoding for a uridine monophosphate kinase protein (umk) comprising the amino acid sequence SEQ ID NO: 3 or SEQ ID NO: 9, wherein the at least one nucleic acid of (ii)-(iii) are linked by a nucleic acid encoding a cleavable Foot-and-Mouth-Disease virus (FMDV) 2 A peptide, thereby encoding the amino acid sequence set forth in SEQ ID NO: 10.

13. The method according to claim 1, wherein said gemcitabine is administrated at a dose of equal or less than 750 mg/m$^2$ per day.

* * * * *

SEQUENCE LISTING

```
<160> NUMBER OF SEQ ID NOS: 11

<210> SEQ ID NO 1
<211> LENGTH: 369
<212> TYPE: PRT
<213> ORGANISM: Homo sapiens

<400> SEQUENCE: 1

Met Asp Met Ala Asp Glu Pro Leu Asn Gly Ser His Thr Trp Leu Ser
1               5                   10                  15

Ile Pro Phe Asp Leu Asn Gly Ser Val Val Ser Thr Asn Thr Ser Asn
                20                  25                  30

Gln Thr Glu Pro Tyr Tyr Asp Leu Thr Ser Asn Ala Val Leu Thr Phe
            35                  40                  45

Ile Tyr Phe Val Val Cys Ile Ile Gly Leu Cys Gly Asn Thr Leu Val
        50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
                100                 105                 110

Ala Ile Cys Arg Val Val Met Thr Val Asp Gly Ile Asn Gln Phe Thr
            115                 120                 125

Ser Ile Phe Cys Leu Thr Val Met Ser Ile Asp Arg Tyr Leu Ala Val
        130                 135                 140

Val His Pro Ile Lys Ser Ala Lys Trp Arg Arg Pro Arg Thr Ala Lys
145                 150                 155                 160

Met Ile Thr Met Ala Val Trp Gly Val Ser Leu Leu Val Ile Leu Pro
                165                 170                 175

Ile Met Ile Tyr Ala Gly Leu Arg Ser Asn Gln Trp Gly Arg Ser Ser
            180                 185                 190

Cys Thr Ile Asn Trp Pro Gly Glu Ser Gly Ala Trp Tyr Thr Gly Phe
        195                 200                 205

Ile Ile Tyr Thr Phe Ile Leu Gly Phe Leu Val Pro Leu Thr Ile Ile
    210                 215                 220

Cys Leu Cys Tyr Leu Phe Ile Ile Ile Lys Val Lys Ser Ser Gly Ile
225                 230                 235                 240

Arg Val Gly Ser Ser Lys Arg Lys Lys Ser Glu Lys Lys Val Thr Arg
                245                 250                 255

Met Val Ser Ile Val Val Ala Val Phe Ile Phe Cys Trp Leu Pro Phe
            260                 265                 270

Tyr Ile Phe Asn Val Ser Ser Val Ser Met Ala Ile Ser Pro Thr Pro
        275                 280                 285

Ala Leu Lys Gly Met Phe Asp Phe Val Val Leu Thr Tyr Ala Asn
    290                 295                 300

Ser Cys Ala Asn Pro Ile Leu Tyr Ala Phe Leu Ser Asp Asn Phe Lys
305                 310                 315                 320
```

```
Lys Ser Phe Gln Asn Val Leu Cys Leu Val Lys Val Ser Gly Thr Asp
            325                 330                 335

Asp Gly Glu Arg Ser Asp Ser Lys Gln Asp Lys Ser Arg Leu Asn Glu
            340                 345                 350

Thr Thr Glu Thr Gln Arg Thr Leu Leu Asn Gly Asp Leu Gln Thr Ser
            355                 360                 365

Ile

<210> SEQ ID NO 2
<211> LENGTH: 260
<212> TYPE: PRT
<213> ORGANISM: Homo sapiens

<400> SEQUENCE: 2

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
    50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Arg Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Asp Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 3
<211> LENGTH: 228
<212> TYPE: PRT
<213> ORGANISM: Homo sapiens

<400> SEQUENCE: 3
```

```
Met Leu Ser Arg Cys Arg Ser Gly Leu Leu His Val Leu Gly Leu Ser
1               5                   10                  15

Phe Leu Leu Gln Thr Arg Arg Pro Ile Leu Leu Cys Ser Pro Arg Leu
            20                  25                  30

Met Lys Pro Leu Val Val Phe Val Leu Gly Gly Pro Gly Ala Gly Lys
        35                  40                  45

Gly Thr Gln Cys Ala Arg Ile Val Glu Lys Tyr Gly Tyr Thr His Leu
    50                  55                  60

Ser Ala Gly Glu Leu Leu Arg Asp Glu Arg Lys Asn Pro Asp Ser Gln
65                  70                  75                  80

Tyr Gly Glu Leu Ile Glu Lys Tyr Ile Lys Glu Gly Lys Ile Val Pro
                85                  90                  95

Val Glu Ile Thr Ile Ser Leu Leu Lys Arg Glu Met Asp Gln Thr Met
            100                 105                 110

Ala Ala Asn Ala Gln Lys Asn Lys Phe Leu Ile Asp Gly Phe Pro Arg
        115                 120                 125

Asn Gln Asp Asn Leu Gln Gly Trp Asn Lys Thr Met Asp Gly Lys Ala
130                 135                 140

Asp Val Ser Phe Val Leu Phe Phe Asp Cys Asn Asn Glu Ile Cys Ile
145                 150                 155                 160

Glu Arg Cys Leu Glu Arg Gly Lys Ser Ser Gly Arg Ser Asp Asp Asn
                165                 170                 175

Arg Glu Ser Leu Glu Lys Arg Ile Gln Thr Tyr Leu Gln Ser Thr Lys
            180                 185                 190

Pro Ile Ile Asp Leu Tyr Glu Glu Met Gly Lys Val Lys Lys Ile Asp
        195                 200                 205

Ala Ser Lys Ser Val Asp Glu Val Phe Asp Glu Val Val Gln Ile Phe
210                 215                 220

Asp Lys Glu Gly
225

<210> SEQ ID NO 4
<211> LENGTH: 346
<212> TYPE: PRT
<213> ORGANISM: Mus musculus

<400> SEQUENCE: 4

Met Glu Met Ser Ser Glu Gln Leu Asn Gly Ser Gln Val Trp Val Ser
1               5                   10                  15

Ser Pro Phe Asp Leu Asn Gly Ser Leu Gly Pro Ser Asn Gly Ser Asn
            20                  25                  30

Gln Thr Glu Pro Tyr Tyr Asp Met Thr Ser Asn Ala Val Leu Thr Phe
        35                  40                  45

Ile Tyr Phe Val Val Cys Val Gly Leu Cys Gly Asn Thr Leu Val
    50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
            100                 105                 110

Ala Ile Cys Arg Val Val Met Thr Val Asp Gly Ile Asn Gln Phe Thr
        115                 120                 125

Ser Ile Phe Cys Leu Thr Val Met Ser Ile Asp Arg Tyr Leu Ala Val
130                 135                 140
```

Val His Pro Ile Lys Ser Ala Lys Trp Arg Arg Pro Arg Thr Ala Lys
145                 150                 155                 160

Met Ile Asn Val Ala Val Trp Cys Val Ser Leu Leu Val Ile Leu Pro
                165                 170                 175

Ile Met Ile Tyr Ala Gly Leu Arg Ser Asn Gln Trp Gly Arg Ser Ser
            180                 185                 190

Cys Thr Ile Asn Trp Pro Gly Glu Ser Gly Ala Trp Tyr Thr Gly Phe
        195                 200                 205

Ile Ile Tyr Ala Phe Ile Leu Gly Phe Leu Val Pro Leu Thr Ile Ile
    210                 215                 220

Cys Leu Cys Tyr Leu Phe Ile Ile Ile Lys Val Lys Ser Ser Gly Ile
225                 230                 235                 240

Arg Val Gly Ser Ser Lys Arg Lys Lys Ser Glu Lys Lys Val Thr Arg
                245                 250                 255

Met Val Ser Ile Val Val Ala Val Phe Ile Phe Cys Trp Leu Pro Phe
            260                 265                 270

Tyr Ile Phe Asn Val Ser Ser Val Ser Val Ala Ile Ser Pro Thr Pro
        275                 280                 285

Ala Leu Lys Gly Met Phe Asp Phe Val Val Ile Leu Thr Tyr Ala Asn
    290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Ala Asp Asn Ser Gln
                325                 330                 335

Ser Gly Ala Glu Asp Ile Ile Ala Trp Val
            340                 345

<210> SEQ ID NO 5
<211> LENGTH: 369
<212> TYPE: PRT
<213> ORGANISM: Rattus norvegicus

<400> SEQUENCE: 5

Met Glu Leu Thr Ser Glu Gln Phe Asn Gly Ser Gln Val Trp Ile Pro
1               5                   10                  15

Ser Pro Phe Asp Leu Asn Gly Ser Leu Gly Pro Ser Asn Gly Ser Asn
                20                  25                  30

Gln Thr Glu Pro Tyr Tyr Asp Met Thr Ser Asn Ala Val Leu Thr Phe
            35                  40                  45

Ile Tyr Phe Val Val Cys Val Val Gly Leu Cys Gly Asn Thr Leu Val
    50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
            100                 105                 110

Ala Ile Cys Arg Val Val Met Thr Val Asp Gly Ile Asn Gln Phe Thr
    115                 120                 125

Ser Ile Phe Cys Leu Thr Val Met Ser Ile Asp Arg Tyr Leu Ala Val
    130                 135                 140

Val His Pro Ile Lys Ser Ala Lys Trp Arg Arg Pro Arg Thr Ala Lys
145                 150                 155                 160

Met Ile Asn Val Ala Val Trp Gly Val Ser Leu Leu Val Ile Leu Pro

```
            165                 170                 175
Ile Met Ile Tyr Ala Gly Leu Arg Ser Asn Gln Trp Gly Arg Ser Ser
            180                 185                 190

Cys Thr Ile Asn Trp Pro Gly Glu Ser Gly Ala Trp Tyr Thr Gly Phe
            195                 200                 205

Ile Ile Tyr Ala Phe Ile Leu Gly Phe Leu Val Pro Leu Thr Ile Ile
            210                 215                 220

Cys Leu Cys Tyr Leu Phe Ile Ile Lys Val Lys Ser Ser Gly Ile
225                 230                 235                 240

Arg Val Gly Ser Ser Lys Arg Lys Ser Glu Lys Lys Val Thr Arg
                    245                 250                 255

Met Val Ser Ile Val Ala Val Phe Ile Phe Cys Trp Leu Pro Phe
                    260                 265                 270

Tyr Ile Phe Asn Val Ser Ser Val Ser Val Ala Ile Ser Pro Thr Pro
            275                 280                 285

Ala Leu Lys Gly Met Phe Asp Phe Val Val Ile Leu Thr Tyr Ala Asn
            290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Val Ser Gly Ala Glu
                    325                 330                 335

Asp Gly Glu Arg Ser Asp Ser Lys Gln Asp Lys Ser Arg Leu Asn Glu
                    340                 345                 350

Thr Thr Glu Thr Gln Arg Thr Leu Leu Asn Gly Asp Leu Gln Thr Ser
            355                 360                 365

Ile

<210> SEQ ID NO 6
<211> LENGTH: 260
<212> TYPE: PRT
<213> ORGANISM: Mus musculus

<400> SEQUENCE: 6

Met Ala Thr Pro Pro Lys Arg Phe Cys Pro Ser Pro Thr Ser Ser
1               5                   10                  15

Glu Gly Thr Arg Ile Lys Lys Ile Ser Ile Glu Gly Asn Ile Ala Ala
                    20                  25                  30

Gly Lys Ser Thr Phe Val Asn Ile Leu Lys Gln Ala Ser Glu Asp Trp
            35                  40                  45

Glu Val Val Pro Glu Pro Val Ala Arg Trp Cys Asn Val Gln Ser Thr
50                  55                  60

Gln Glu Glu Phe Glu Glu Leu Thr Thr Ser Gln Lys Ser Gly Gly Asn
65                  70                  75                  80

Val Leu Gln Met Met Tyr Glu Lys Pro Glu Arg Trp Ser Phe Thr Phe
                    85                  90                  95

Gln Ser Tyr Ala Cys Leu Ser Arg Ile Arg Ala Gln Leu Ala Ser Leu
            100                 105                 110

Asn Gly Lys Leu Lys Asp Ala Glu Lys Pro Val Leu Phe Phe Glu Arg
            115                 120                 125

Ser Val Tyr Ser Asp Arg Tyr Ile Phe Ala Ser Asn Leu Tyr Glu Ser
            130                 135                 140

Asp Cys Met Asn Glu Thr Glu Trp Thr Ile Tyr Gln Asp Trp His Asp
145                 150                 155                 160

Trp Met Asn Ser Gln Phe Gly Gln Ser Leu Glu Leu Asp Gly Ile Ile
```

```
            165                 170                 175
Tyr Leu Arg Ala Thr Pro Glu Lys Cys Leu Asn Arg Ile Tyr Leu Arg
                180                 185                 190

Gly Arg Asn Glu Glu Gln Gly Ile Pro Leu Glu Tyr Leu Glu Lys Leu
            195                 200                 205

His Tyr Lys His Glu Ser Trp Leu Leu His Arg Thr Leu Lys Thr Ser
        210                 215                 220

Phe Asp Tyr Leu Gln Glu Val Pro Val Leu Thr Leu Asp Val Asn Glu
225                 230                 235                 240

Asp Phe Lys Asp Lys His Glu Ser Leu Val Glu Lys Val Lys Glu Phe
                245                 250                 255

Leu Ser Thr Leu
            260

<210> SEQ ID NO 7
<211> LENGTH: 260
<212> TYPE: PRT
<213> ORGANISM: Rattus norvegicus

<400> SEQUENCE: 7

Met Ala Thr Pro Pro Lys Arg Phe Cys Ser Ser Pro Thr Ser Ser
1               5                   10                  15

Glu Gly Thr Arg Ile Lys Lys Ile Ser Ile Glu Gly Asn Ile Ala Ala
                20                  25                  30

Gly Lys Ser Thr Phe Val Asn Ile Leu Lys Gln Val Cys Glu Asp Trp
            35                  40                  45

Glu Val Val Pro Glu Pro Val Ala Arg Trp Cys Asn Val Gln Ser Thr
        50                  55                  60

Gln Asp Glu Phe Glu Glu Leu Thr Thr Ser Gln Lys Ser Gly Gly Asn
65                  70                  75                  80

Val Leu Gln Met Met Tyr Glu Lys Pro Glu Arg Trp Ser Phe Ile Phe
                85                  90                  95

Gln Ser Tyr Ala Cys Leu Ser Arg Ile Arg Ala Gln Leu Ala Ser Leu
            100                 105                 110

Asn Gly Ser Leu Arg Asp Ala Glu Lys Pro Val Leu Phe Phe Glu Arg
        115                 120                 125

Ser Val Tyr Ser Asp Arg Tyr Ile Phe Ala Ser Asn Leu Tyr Glu Ser
130                 135                 140

Asp Cys Met Asn Glu Thr Glu Trp Thr Ile Tyr Gln Asp Trp His Asp
145                 150                 155                 160

Trp Met Asn Ser Gln Phe Gly Gln Ser Leu Glu Leu Asp Gly Ile Ile
                165                 170                 175

Tyr Leu Arg Ala Thr Pro Glu Lys Cys Leu Asn Arg Ile Tyr Ile Arg
            180                 185                 190

Gly Arg Asp Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Glu Tyr Leu Gln Glu Val Pro Ile Leu Thr Leu Asp Val Asn Leu
225                 230                 235                 240

Asp Phe Lys Asp Lys Glu Glu Ser Leu Val Glu Lys Val Lys Glu Phe
                245                 250                 255

Leu Ser Thr Thr
            260
```

<210> SEQ ID NO 8
<211> LENGTH: 260
<212> TYPE: PRT
<213> ORGANISM: Bos taurus

<400> SEQUENCE: 8

```
Met Ala Thr Pro Pro Lys Arg Ser Cys Pro Ser Ala Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Val Cys Glu Asp Trp
        35                  40                  45

Glu Val Val Pro Glu Pro Val Ala Arg Trp Cys Asn Val Gln Ser Thr
50                  55                  60

Gln Asp Glu Phe Glu Glu Leu Thr Thr Ser Gln Lys Ser Gly Gly Asn
65                  70                  75                  80

Val Leu Gln Met Met Tyr Glu Lys Pro Glu Arg Trp Ser Phe Thr Phe
                85                  90                  95

Gln Ser Tyr Ala Cys Leu Ser Arg Ile Arg Ala Gln Leu Ala Ala Leu
            100                 105                 110

Asn Gly Lys Leu Lys Asp Ala Glu Lys Pro Val Leu Phe Phe Glu Arg
        115                 120                 125

Ser Val Tyr Ser Asp Arg Tyr Ile Phe Ala Ser Asn Leu Tyr Glu Ser
130                 135                 140

Asp Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Arg Ala Thr Pro Glu Lys Cys Leu Asn Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys His Asp Ser Leu Ile Glu Lys Val Lys Asp Phe
                245                 250                 255

Leu Ser Thr Leu
            260
```

<210> SEQ ID NO 9
<211> LENGTH: 227
<212> TYPE: PRT
<213> ORGANISM: Rattus norvegicus

<400> SEQUENCE: 9

```
Met Leu Ser Ser Cys Arg Arg Trp Leu Leu His Val Leu Val Pro Ser
1               5                   10                  15

Phe Pro Pro Leu Thr Arg Gly Leu Arg Phe Phe Pro Leu Gln Leu Met
            20                  25                  30

Lys Pro Leu Val Val Phe Val Leu Gly Gly Pro Gly Ala Gly Lys Gly
        35                  40                  45

Thr Gln Cys Ala Arg Ile Val Glu Lys Tyr Gly Tyr Thr His Leu Ser
        50                  55                  60
```

```
Ala Gly Glu Leu Leu Arg Asp Glu Arg Lys Asn Pro Asp Ser Gln Tyr
 65                  70                  75                  80

Gly Glu Leu Ile Glu Lys Tyr Ile Lys Glu Gly Lys Ile Val Pro Val
                 85                  90                  95

Glu Ile Thr Ile Ser Leu Leu Lys Arg Glu Met Asp Gln Thr Met Ala
            100                 105                 110

Ala Asn Ala Gln Lys Asn Lys Phe Leu Ile Asp Gly Phe Pro Arg Asn
        115                 120                 125

Gln Asp Asn Leu Gln Gly Trp Asn Lys Thr Met Asp Gly Lys Ala Asp
130                 135                 140

Val Ser Phe Val Leu Phe Phe Asp Cys Asn Asn Glu Ile Cys Ile Asp
145                 150                 155                 160

Arg Cys Leu Glu Arg Gly Lys Ser Ser Gly Arg Ser Asp Asp Asn Arg
                165                 170                 175

Glu Ser Leu Glu Lys Arg Ile Gln Thr Tyr Leu Glu Ser Thr Lys Pro
            180                 185                 190

Ile Ile Asp Leu Tyr Glu Met Gly Lys Val Lys Lys Ile Asp Ala
        195                 200                 205

Ser Lys Ser Val Asp Glu Val Phe Gly Asp Val Met Lys Ile Phe Asp
210                 215                 220

Lys Glu Gly
225

<210> SEQ ID NO 10
<211> LENGTH: 507
<212> TYPE: PRT
<213> ORGANISM: Artificial sequence
<220> FEATURE:
<223> OTHER INFORMATION: Fusion DCK:UMK

<400> SEQUENCE: 10

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
 50                  55                  60

Gln Asp Glu Phe Glu Glu Leu Thr Met Ser Gln Lys Asn Gly Gly Asn
 65                  70                  75                  80

Val Leu Gln Met Met Tyr Glu Lys Pro Glu Arg Trp Ser Phe Thr Phe
                 85                  90                  95

Gln Thr Tyr Ala Cys Leu Ser Arg Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Asp Arg Tyr Ile Phe Ala Ser Asn Leu Tyr Glu Ser
130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190
```

```
Gly Arg Asn Glu Glu Gln Gly Ile Pro Leu Glu Tyr Leu Glu Lys Leu
            195                 200                 205

His Tyr Lys His Glu Ser Trp Leu Leu His Arg Thr Leu Lys Thr Asn
        210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu Gln Leu Leu Asn Pro Asp Leu Leu Lys Leu Ala Gly
            260                 265                 270

Asp Val Glu Ser Asn Pro Gly Met Leu Ser Arg Cys Arg Ser Gly Leu
        275                 280                 285

Leu His Val Leu Gly Leu Ser Phe Leu Leu Gln Thr Arg Arg Pro Ile
290                 295                 300

Leu Leu Cys Ser Pro Arg Leu Met Lys Pro Leu Val Val Phe Val Leu
305                 310                 315                 320

Gly Gly Pro Gly Ala Gly Lys Gly Thr Gln Cys Ala Arg Ile Val Glu
                325                 330                 335

Lys Tyr Gly Tyr Thr His Leu Ser Ala Gly Glu Leu Leu Arg Asp Glu
            340                 345                 350

Arg Lys Asn Pro Asp Ser Gln Tyr Gly Glu Leu Ile Glu Lys Tyr Ile
        355                 360                 365

Lys Glu Gly Lys Ile Val Pro Val Glu Ile Thr Ile Ser Leu Leu Lys
    370                 375                 380

Arg Glu Met Asp Gln Thr Met Ala Ala Asn Gln Lys Asn Lys Phe
385                 390                 395                 400

Leu Ile Asp Gly Phe Pro Arg Asn Gln Asp Asn Leu Gln Gly Trp Asn
                405                 410                 415

Lys Thr Met Asp Gly Lys Ala Asp Val Ser Phe Val Leu Phe Phe Asp
            420                 425                 430

Cys Asn Asn Glu Ile Cys Ile Glu Arg Cys Leu Glu Arg Gly Lys Ser
        435                 440                 445

Ser Gly Arg Ser Asp Asp Asn Arg Glu Ser Leu Glu Lys Arg Ile Gln
450                 455                 460

Thr Tyr Leu Gln Ser Thr Lys Pro Ile Ile Asp Leu Tyr Glu Glu Met
465                 470                 475                 480

Gly Lys Val Lys Lys Ile Asp Ala Ser Lys Ser Val Asp Glu Val Phe
                485                 490                 495

Asp Glu Val Val Gln Ile Phe Asp Lys Glu Gly
            500                 505

<210> SEQ ID NO 11
<211> LENGTH: 7548
<212> TYPE: DNA
<213> ORGANISM: Artificial sequence
<220> FEATURE:
<223> OTHER INFORMATION: Vector pHNeo Sst2 DCK:UMK

<400> SEQUENCE: 11
cctgcaggcg ttacataact tacggtaaat ggcccgcctg gctgaccgcc caacgacccc      60
cgcccattga cgtcaataat gacgtatgtt cccatagtaa cgccaatagg gactttccat     120
tgacgtcaat gggtggagta tttacggtaa actgcccact tggcagtaca tcaagtgtat     180
catatgccaa gtacgccccc tattgacgtc aatgacggta aatggcccgc ctggcattat     240
gcccagtaca tgaccttatg ggactttcct acttggcagt acatctacgt attagtcatc     300
```

```
gctattacca tgatgatgcg gttttggcag tacatcaatg ggcgtggata gcggtttgac      360
tcacggggat ttccaagtct ccaccccatt gacgtcaatg ggagtttgtt ttgactagtc      420
gcgtcgtgca ggacgtgaca aatctagtcg cgtcgtgcag gacgtgacaa atctagtcgc      480
gtcgtgcagg acgtgacaat ctagttaccg gcggaaacgg tctcggggttg agaggtcacc     540 cgagggacag gcagctgctg aaccaatagg accggcgcac agggcggatg ctgcccctca      600
ttggcggccg ttgagagtga ccaagagcca atgagtcagc cgggggggcg tagcagtgac      660
gtaagttgcg gaggaggccg cttcgaatcg gcagcggcca gcttggtggc atggaccaat      720
cagcgtcctc caacgaggag cgccttcgcc aatcggaggc tccacgacgg ggctggggg       780 gagggtatat aagccgagtc ggcggcggcg cgctccacac gggccgagac cacagcgacg      840
ggagcgtctg cctctgcggg gccgagaggt aagcgccgcg gcctgcccctt tccaggccaa     900 ctcggagccc gtctcgtggc tccgcctgat cgggggctcc tgtcgccctc agatcggtcg      960
gaacgccgtc gcgctccggg actacaagcc tgttgctggg cccggagact gccgaaggac     1020
cgctgagcac tgtcctcagc gccggcacca tggccacccc gcccaagaga agctgcccgt     1080 cttttctcagc cagctctgag gggacccgca tcaagaaaat ctccatcgaa gggaacatcg    1140
ctgcagggaa gtcaacattt gtgaatatcc ttaaacaatt gtgtgaagat tgggaagtgg     1200
ttcctgaacc tgttgccaga tggtgcaatg ttcaaagtac tcaagatgaa tttgaggaac     1260
ttacaatgtc tcagaaaaat ggtgggaatg ttcttcagat gatgtatgag aaacctgaac     1320
gatggtcttt taccttccaa acatatgcct gtctcagtcg aataagagct cagcttgcct     1380
ctctgaatgg caagctcaaa gatgcagaga aacctgtatt atttttttgaa cgatctgtgt    1440 atagtgacag gtatattttt gcatctaatt tgtatgaatc tgaatgcatg aatgagacag     1500
agtggacaat ttatcaagac tggcatgact ggatgaataa ccaatttggc caaagccttg     1560
aattggatgg aatcatttat cttcaagcca ctccagagac atgcttacat agaatatatt     1620
tacggggaag aaatgaagag caaggcattc ctcttgaata tttagagaag cttcattata     1680
aacatgaaag ctggctcctg cataggacac tgaaaaccaa cttcgattat cttcaagagg     1740
tgcctatctt aacactggat gttaatgaag actttaaaga caaatatgaa agtctggttg     1800
aaaaggtcaa agagttttttg agtactttgg taccacagct gctcaacttt gacctgctca     1860
agctggctgg ggatgtggag agcaaccctg ggcccatcat gaagccgctg gtcgtgttcg     1920
tcctcggcgg ccccggcgcc ggcaagggga cccagtgcgc ccgcatcgtc gagaaatatg     1980
gctacacaca ccttttctgca ggagagctgc ttcgtgatga aaggaagaac ccagattcac    2040
agtatggtga acttattgaa aagtacatta agaaggaaa gattgtacca gttgagataa      2100
ccatcagttt attaaagagg gaaatggatc agacaatggc tgccaatgct cagaagaata     2160
aattcttgat tgatgggttt ccaagaaatc aagacaacct tcaaggatgg aacaagacca     2220
tggatgggaa ggcagatgta tctttcgttc tcttttttga ctgtaataat gagatttgta     2280
ttgaacgatg tcttgagagg ggaaagagta gtggtaggag tgatgacaac agagagagct     2340
tggaaaagag aattcagacc taccttcagt caacaaagcc aattattgac ttatatgaag     2400
aaatggggaa agtcaagaaa atagatgctt ctaaatctgt tgatgaagtt tttgatgaag     2460
ttgtgcagat ttttgacaag gaaggctaag ctagctggcc agacatgata agatacattg     2520
atgagtttgg acaaaccaca actagaatgc agtgaaaaaa atgctttatt tgtgaaattt     2580
gtgatgctat tgctttattt gtaaccatta taagctgcaa taaacaagtt aacaacaaca     2640
```

```
attgcattca tttatgttt caggttcagg gggaggtgtg ggaggttttt taaagcaagt    2700
aaaacctcta caaatgtggt atggaaatgt taattaacta gccatgacca aaatcccta    2760
acgtgagttt tcgttccact gagcgtcaga ccccgtagaa aagatcaaag gatcttcttg    2820
agatccttt tttctgcgcg taatctgctg cttgcaaaca aaaaaccac cgctaccagc    2880
ggtggtttgt ttgccggatc aagagctacc aactcttttt ccgaaggtaa ctggcttcag    2940
cagagcgcag ataccaaata ctgttcttct agtgtagccg tagttaggcc accacttcaa    3000
gaactctgta gcaccgccta catacctcgc tctgctaatc ctgttaccag tggctgctgc    3060
cagtggcgat aagtcgtgtc ttaccgggtt ggactcaaga cgatagttac cggataaggc    3120
gcagcggtcg ggctgaacgg ggggttcgtg cacacagccc agcttggagc gaacgaccta    3180
caccgaactg agatacctac agcgtgagct atgagaaagc gccacgcttc cgaagggag    3240
aaaggcggac aggtatccgg taagcggcag ggtcggaaca ggagagcgca cgagggagct    3300
tccaggggga aacgcctggt atctttatag tcctgtcggg tttcgccacc tctgacttga    3360
gcgtcgattt ttgtgatgct cgtcaggggg gcggagccta tggaaaaacg ccagcaacgc    3420
ggccttttta cggttcctgg ccttttgctg gccttttgct cacatgttct taattaacct    3480
gcagggcctg aaataacctc tgaaagagga acttggttag gtaccttctg aggctgaaag    3540
aaccagctgt ggaatgtgtg tcagttaggg tgtggaaagt ccccaggctc cccagcaggc    3600
agaagtatgc aaagcatgca tctcaattag tcagcaacca ggtgtggaaa gtccccaggc    3660
tccccagcag gcagaagtat gcaaagcatg catctcaatt agtcagcaac catagtccca    3720
ctagtacacg tgggttcccg cacgtccgct gggctccac tctgacgtga ttctagtttc    3780
atcaccaccg ccaccccccc gccccccgc catctgaaag ggttctaggg gatttgcaac    3840
ctctctcgtg tgtttcttct ttccgagaag cgccgccaca cgagaaagct ggccgcgaaa    3900
gtcgtgctgg aatcacttcc aacgaaaccc caggcataga tgggaaaggg tgaagaacac    3960
gttgtcatgg ctaccgtttc cccggtcacg gaataaacgc tctctaggat ccggaagtag    4020
ttccgccgcg acctctctaa aaggatggat gtgttctctg cttacattca ttggacgttt    4080
tcccttagag gccaaggccg cccaggcaaa ggggcggtcc cacgcgtgag gggcccgcgg    4140
agccatttga ttggagaaaa gctgcaaacc ctgaccaatc ggaaggagcc acgcttcggg    4200
catcggtcac cgcacctgga cagctccgat tggtggactt ccgccccccc tcacgaatcc    4260
tcattgggtg ccgtgggtgc gtggtgcggc gcgattggtg ggttcatgtt tcccgtcccc    4320
cgcccgcgag aagtgggggt gaaaagcggc ccgacctgct tggggtgtag tgggcggacc    4380
gcgcggctgg aggtgtgagg atccgaaccc aggggtgggg ggtggaggcg gctcctgcga    4440
tcgaagggga cttgagactc accggtacca ccatggacat ggcggatgag ccactcaatg    4500
gaagccacac atggctatcc attccatttg acctcaatgg ctctgtggtg tcaaccaaca    4560
cctcaaacca gacagagccg tactatgacc tgacaagcaa tgcagtcctc acattcatct    4620
attttgtggt ctgcatcatt gggttgtgtg caacacact tgtcatttat gtcatcctcc    4680
gctatgccaa gatgaagacc atcaccaaca tttacatcct caacctggcc atcgcagatg    4740
agctcttcat gctgggtctg ccttttcttgg ctatgcaggt ggctctggtc cactggccct    4800
ttggcaaggc catttgccgg gtggtcatga ctgtggatgg catcaatcag ttcaccagca    4860
tcttctgcct gacagtcatg agcatcgacc gataccctgg tgtggtccac cccatcaagt    4920
cggccaagtg gaggagaccc cggacggcca agatgatcac catggctgtg tggggagtct    4980
ctctgctggt catcttgccc atcatgatat atgctgggct ccggagcaac cagtggggga    5040
```

```
gaagcagctg caccatcaac tggccaggtg aatctggggc ttggtacaca gggttcatca    5100
tctacacttt cattctgggg ttcctggtac ccctcaccat catctgtctt tgctacctgt    5160
tcattatcat caaggtgaag tcctctggaa tccgagtggg ctcctctaag aggaagaagt    5220
ctgagaagaa ggtcacccga atggtgtcca tcgtggtggc tgtcttcatc ttctgctggc    5280
ttcccttcta catattcaac gtttcttccg tctccatggc catcagcccc accccagccc    5340
ttaaaggcat gtttgacttt gtggtggtcc tcacctatgc taacagctgt gccaaccctg    5400
tcctatatgc cttcttgtct gacaacttca agaagagctt ccagaatgtc tctgcttgg     5460 tcaaggtgag cggcacagat gatggggagc ggagtgacag taagcaggac aaatcccggc    5520
tgaatgagac cacggagacc cagaggaccc tcctcaatgg agacctccaa accagtatct    5580
gaagctagga gcaggtttcc ccaatgacac aaaacgtgca acttgaaact ccgcctggtc    5640
tttccaggtc tagaggggta acactttgta ctgcgtttgg ctccacgctc gatccactgg    5700
cgagtgttag taacagcact gttgcttcgt agcggagcat gacggccgtg ggaactcctc    5760
cttggtaaca aggacccacg gggccaaaag ccacgcccac acgggcccgt catgtgtgca    5820
accccagcac ggcgacttta ctgcgaaacc cactttaaag tgacattgaa actggtaccc    5880
acacactggt gacaggctaa ggatgcccct caggtacccc gaggtaacac gcgacactcg    5940
ggatctgaga aggggactgg ggcttctata aaagcgctcg gtttaaaaag cttctatgcc    6000
tgaataggtg accggaggtc ggcacctttc ctttgcaatt actgacccta tgaatacaac    6060
tgactgtttg acaattaatc atcggcatag tatatcggca tagtataata cgactcacta    6120
taggagggcc accatgattg aacaagatgg attgcacgca ggttctccgg ccgcttgggt    6180
ggagaggcta ttcggctatg actgggcaca acagacaatc ggctgctctg atgccgccgt    6240
gttccggctg tcagcgcagg ggcgcccggt tctttttgtc aagaccgacc tgtccggtgc    6300
cctgaatgaa ctgcaggacg aggcagcgcg gctatcgtgg ctggccacga cgggcgttcc    6360
ttgcgcagct gtgctcgacg ttgtcactga agcgggaagg gactggctgc tattgggcga    6420
agtgccgggg caggatctcc tgtcatctca ccttgctcct gccgagaaag tatccatcat    6480
ggctgatgca atgcggcggc tgcatacgct tgatccggct acctgcccat tcgaccacca    6540
agcgaaacat cgcatcgagc gagcacgtac tcggatggaa gccggtcttg tcgatcagga    6600
tgatctggac gaagagcatc aggggctcgc gccagccgaa ctgttcgcca ggctcaaggc    6660
gcgcatgccc gacggcgagg atctcgtcgt gacccatggc gatgcctgct tgccgaatat    6720
catggtggaa aatggccgct tttctggatt catcgactgt ggccggctgg gtgtggcgga    6780
ccgctatcag gacatagcgt tggctacccg tgatattgct gaagagcttg gcggcgaatg    6840
ggctgaccgc ttcctcgtgc tttacggtat cgccgctccc gattcgcagc gcatcgcctt    6900
ctatcgcctt cttgacgagt tcttctgagc gggactctgg ggttcgaaat gaccgaccaa    6960
gcgaattcgc tagcattatc cctaatacct gccaccccac tcttaatcag tggtggaaga    7020
acggtctcag aactgtttgt ttcaattggc catttaagtt tagtagtaaa agactggtta    7080
atgataacaa tgcatcgtaa aaccttcaga aggaaaggag aatgttttgt ggaccacttt    7140
ggttttcttt tttgcgtgtg gcagttttaa gttattagtt tttaaaatca gtactttttta   7200 atggaaacaa cttgaccaaa aatttgtcac agaattttga gacccattaa aaaagttaaa    7260
tgagaaacct gtgtgttcct ttggtcaaca ccgagacatt taggtgaaag acatctaatt    7320
ctggttttac gaatctggaa acttcttgaa aatgtaattc ttgagttaac acttctgggt    7380
```

-continued

| | | | | |
|---|---|---|---|---|
| ggagaatagg | gttgttttcc | ccccacataa | ttggaagggg aaggaatatc | atttaaagct 7440 |
| atgggagggt | tgctttgatt | acaacactgg | agagaaatgc agcatgttgc | tgattgcctg 7500 |
| tcactaaaac | aggccaaaaa | ctgagtcctt | gggttgcata gaaagctg | 7548 |